United States Patent [19]

Danielson

[11] Patent Number: 5,541,510
[45] Date of Patent: Jul. 30, 1996

[54] MULTI-PARAMETER EDDY CURRENT MEASURING SYSTEM WITH PARAMETER COMPENSATION TECHNICAL FIELD

[75] Inventor: Tim Danielson, Monument, Colo.

[73] Assignee: Kaman Instrumentation Corporation, Colorado Spring, Colo.

[21] Appl. No.: 417,748

[22] Filed: Apr. 6, 1995

[51] Int. Cl.[6] .......................... G01R 33/12; G01N 27/72; G01B 7/06; G01B 7/14
[52] U.S. Cl. ............... 324/233; 324/207.16; 324/207.26; 324/225; 324/227; 324/229; 324/234
[58] Field of Search ..................... 324/225, 227, 324/229–234, 236–238, 207.12, 207.16, 207.18, 207.19, 207.26, 654–657

[56] References Cited

U.S. PATENT DOCUMENTS

| | | | |
|---|---|---|---|
| 2,928,043 | 3/1960 | Foerster | 324/238 |
| 2,939,073 | 5/1960 | Eul, Jr. | 324/238 |
| 3,358,225 | 12/1967 | Peugeot | 324/225 |
| 3,496,458 | 2/1970 | Bromley | 324/40 |
| 3,619,805 | 11/1971 | Bean | 331/65 |
| 3,718,855 | 2/1973 | Rogel et al. | 324/37 |
| 4,109,199 | 8/1978 | Ball et al. | 324/202 |
| 4,186,792 | 2/1980 | Yamada et al. | 164/150 |
| 4,215,310 | 7/1980 | Schwerer, III | 324/225 |
| 4,290,017 | 9/1981 | Fortunko | 324/237 |
| 4,314,203 | 2/1982 | Häberlien | 324/262 |
| 4,438,754 | 3/1984 | Nanny et al. | 125/14 |
| 4,596,953 | 6/1986 | Nagasaka et al. | 324/242 |
| 4,644,271 | 2/1987 | Toth et al. | 324/238 |
| 4,644,274 | 2/1987 | Casarcia | 324/262 |
| 4,673,877 | 6/1987 | Sakamoto et al. | 324/225 |
| 4,727,322 | 2/1988 | Lonchampt et al. | 324/229 |
| 4,755,753 | 7/1988 | Chern | 324/237 |
| 4,814,702 | 3/1989 | Driggers et al. | 324/207 |
| 4,816,759 | 3/1989 | Ames et al. | 324/207 |
| 4,829,250 | 5/1989 | Rotier | 324/225 |
| 4,849,693 | 7/1989 | Prince et al. | 324/225 |
| 4,864,235 | 9/1989 | Tornblom | 324/233 |
| 4,922,201 | 5/1990 | Vernon et al. | 324/225 X |
| 4,924,182 | 5/1990 | Vernon et al. | 324/225 X |
| 5,394,084 | 2/1995 | Snyder | 324/233 X |

OTHER PUBLICATIONS

Thichness and Conductivity of Metallic Layers from eddy Current Measurements by John C. Moulder, Erol Uzal, and James H. Rose, Rev. Sci. Intrum., vol. 63, No. 6, Jun. 1992.
Analytical Solutions to Eddy–Current Probe–Coil Problems by C. V. Dodd and W. E. Deeds, Journal of Applird Physics, vol. 39, No. 6, May 1968.
Thickness Measurements Using Eddy–Current Techniques by C. V. Dodds and W. A. Simpson, Jr., Oak Ridge National Laboratory, Oak Ridge, Tennessee, Mar. 1972.

Primary Examiner—Gerard R. Strecker
Attorney, Agent, or Firm—McCormick, Pauling & Huber

[57] ABSTRACT

This invention uses a single eddy current coil to measure multiple parameters of conductive target simultaneously using a single fixed frequency. For example, the system consisting of the sensor coil, connecting cable, and signal conditioning electronics, can measure the thickness of a target and the distance of the target from the coil. Alternatively, it could simultaneously measure the distance of the target to the coil, i.e. lift-off, and one of the electrical properties of the target, such as the resistivity. The present system is useful in material characterization of targets where the lift-off information can be used to correct for any lift-off induced error in the apparent resistivity. In general, it can determine any pair of two characteristics of the target/sensor relationship simultaneously. This invention provides significant improvement in accuracy and flexibility of eddy current sensors and can be manufactured at a low cost due to the use of a single coil and a single fixed frequency in the signal conditioning electronics. An alternative sensor configuration utilizing two sensors differentially to produce a cladding insensitive—displacement measurement is also contemplated by the present invention.

21 Claims, 4 Drawing Sheets

MULTI-PARAMETER EDDY CURRENT MEASURING SYSTEM WITH PARAMETER COMPENSATION TECHNICAL FIELD

TECHNICAL FIELD

This invention relates generally to eddy current sensing devices, and more specifically to a system that employs a single coil to simultaneously measure multiple parameters of a conductive workpiece.

BACKGROUND OF THE INVENTION

Eddy current sensors are well known in the art. These devices are used in a variety of situations where non-contact measurements for parameters such as separation or electrical resistance are desired. Eddy current sensors have been utilized to measure displacement, electrical properties and other physical characteristics of material such as thickness or flaws that modify the apparent electrical characteristics. One such application is the measurement of runout in magnetic steel rollers. Eddy current sensor systems have been used to measure the runout in the rollers but accuracy is limited because of sensitivity to permeability changes that are typical in such rollers. Thickness measurement of aluminum cans during formation is another application. In the can making process, a carbide punch is used to draw an aluminum cup through a series of dies to form a finished can body. The centerline position of the punch can affect the real thickness of the cans and, in prior art systems, affect the apparent thickness of the cans.

Sensing thickness using eddy currents has been accomplished by prior art systems including those which adjust circuit impedances such that the system is insensitive to distance. The system typically utilizes a classic three coil eddy current setup with a driver coil and two pickup coils. The driver coil excites the material with an AC magnetic field and the pick up coils see an impedance change caused by eddy currents induced in the material. Because this technique uses three coils, it is comparatively expensive to produce and is still sensitive to errors from lift-off (sensor—workpiece separation) if not operated within a limited range. Other systems use eddy current sensors to detect cladding thickness with a single coil, but are sensitive to lift-off errors as well. Systems with multiple frequencies have been developed to distinguish thickness changes from other effects, but dual frequencies require expensive and complex circuitry to implement.

Still others systems have measured thickness by means of eddy current devices and have used the orthogonal impedance outputs of an eddy current sensor to determine lift-off from the workpiece surface and compensate for the same. Lift-off errors have been corrected by physically moving the sensor to a specific impedance and measuring its orthogonal impedance component. However, this design has several intrinsic problems. For example, a servo system must physically position the sensor; a requirement which severely hampers the usefulness of the device as it cannot be used at high speed, cannot be placed in restrictive locations, and imposes severe environmental constraints on the use of the device. Moreover, the impedance signal components (real and imaginary) must be completely orthogonal for proper operation.

In general, known devices are capable of measuring a single parameter and are usually configured with one parameter being dependent on another. For example, the apparatus and method disclosed in U.S. Pat. No. 4,290,017 has an oscillator with an amplifier for supplying gain, a feed back loop linking the input and output of the amplifier and a two port ferromagnetic resonator connected within the loop to modulate the level and frequency of the oscillator signal in response to eddy currents induced in the surface of a workpiece sample. There is a variable attenuator connected within the feedback loop to adjust the power level of the oscillator, and an adjustable phase shifter for changing the total phase shift of the signal within the loop. There is also a probe connected to the circuit in a transition mode which is adapted to respond to the electro-magnetic field generated by the eddy currents. The probe includes a ferromagnetic crystal, with an outer circuit loop encircling the crystal and an inner circuit loop encircling the crystal orthogonal to the outer loop. The '017 device permits the measurement of changes in both the magnitude and phase of that system's signal; allowing for independent measurement of the real and imaginary parts of the impedance of the circuit.

U.S. Pat. No. 4,727,322 discloses a method and apparatus for measuring a system parameter such as workpiece thickness by means of eddy currents generated in the workpiece as a result of the proximity of a probe to the surface. The sensor in the probe measures two orthogonal components of the complex impedance. In operation, the '322 sensor is moved towards the workpiece until one component of the impedance reaches a pre-determined value and the characteristic value is measured as a value of the other component. The first component is selected during calibration as that component which is most sensitive to variation in distance between the sensor and the workpiece.

The apparatus disclosed in U.S. Pat. No. 3,358,225 details a lift-off compensation technique for eddy current testers. The '225 apparatus includes an impedance bridge having a signal generator operating at a constant frequency and voltage. The '225 apparatus is used to compare the impedance of an eddy current probe positioned in proximity to a conductive sample with a standard impedance associated with the probe to provide separated outputs of reactive and resistive components of unbalance of the impedance bridge. The '225 apparatus includes a mechanism for selecting a pre-determined portion of one of the outputs and combining it with the other output to provide a signal which is coupled to a read out device for indicating the thickness of the sample workpiece under inspection.

Eddy current non-contacting sensors also include the non-contacting displacement transducer found in U.S. Pat. No. 3,619,805 and the eddy current surface mapping system for workpiece flaw detection shown in U.S. Pat. No. 4,755,753. The eddy current flaw detection system of U.S. Pat. No. 3,718,855 and 3,496,458 rely on a single coil in a sensor probe for detection. Other single probe devices are found in U.S. Pat. No. 4,644,274 for an apparatus that supports an eddy current probe used to scan an irregular surface. The electromagnetic system found in U.S. Pat. No. 4,438,754 is used for sensing and remotely controlling the spatial relationship between a tool and workpiece. The '754 system relies on magnetic devices positioned in an opposed relationship with respect to the tool and a workpiece surface such that the magnetic flux passes between the magnetic elements through the surface.

The systems of the prior art are generally burdened by the need for multiple coils, frequencies or are not capable of simultaneous measurement of different parameters, such as material thickness and separation. It would be desirable to have an eddy current system that employs only a single coil and is capable of simultaneously measuring two parameters. The present system is drawn towards such an invention.

SUMMARY OF INVENTION

An object of the present invention is to provide a measurement system to simultaneously measure two parameters (e.g., thickness and displacement) with a single eddy current sensor coil operating at a single fixed frequency.

Another object of the present invention is to provide a system of the foregoing type which is relatively insensitive to variations in the electrical properties of a material.

Still another aspect of the present invention is to provide a system of the foregoing type which system output signals map to unique points in a system impedance plane.

Yet another object of the present invention is to provide a system of the foregoing type which orthogonalizes electrical output signals to allow for the detection of more than one variable.

Still another aspect of the present invention is to provide a system of the foregoing type capable of sensing temperature and used as a correction factor for other measured parameters.

Another aspect of the present invention is to provide a system of the foregoing type that allows the measurements to be made with a single sensor, in a limited space, in a hostile environment, with relatively simple electronics, and still maintain good sensitivity to the measurement parameters.

According to the present invention, a method of measuring physical parameters characteristic of a workpiece whose parameters include material, thickness, temperature, permeability and conductivity includes the steps of providing an excitation circuit having electrical components that characterize system electrical parameters, the excitation circuit further having an excitation circuit impedance defined by said system electrical parameters. The method also includes the step of providing a sensor having an electrical coil at a preselected diameter. The coil is positioned at a selected separation distance from the workpiece. Presented to the coil is an excitation signal at a single preselected angular frequency selected such that an effective product of the workpiece permeability and resistivity and the separation distance map to a single point in an excitation circuit impedance plane. The method also includes the steps of measuring a voltage magnitude of the excitation signal; measuring a phase of the excitation signal, generating signals indicative of the single excitation circuit impedance plane point; and generating signals indicative of a computed value of a desired one or more of the parameters.

DESCRIPTION OF THE PREFERRED EMBODIMENT

As noted above, Eddy current sensors have been used for a variety of applications, but in general they are designed to be sensitive to one specific parameter such as distance. The present invention, senses multiple parameters such as thickness and distance simultaneously and uses the result of one measurement to correct for undesirable sensitivities in another measurement. Advantages of the present invention include the use of a single low cost sensor coil and the avoidance of switching sensor frequencies. Moreover, the present system has the ability to compensate one parameter value for changes in the value of another parameter; resulting in greater accuracy. It should be noted that temperature can also be sensed, and therefore used as a tertiary correction factor for other parameters.

In general, there are three main parameters to be sensed by the present system: electrical properties, thickness, and distance. Eddy current sensors are essentially governed by a constant expressed as the product of $r^2\omega\mu\sigma$. The parameter 'r' is the mean radius of the coil which can vary in design, but is constant in an application. The parameter '$\omega$' is the radial frequency of the current or voltage used to excite the coil and can be varied in an application, but in general is constant as the associated circuitry is simpler. The parameters "$\mu,\sigma$" are, respectively, the permeability and conductivity of the material. It is important to note that the effective conductivity of a material as seen by an eddy current sensor can change depending on the thickness of the target material or target geometry. The thickness of the material can thus be determined if the actual $\mu$ and $\sigma$ values are constant.

The present system measures thickness without the need for the classic three coil configuration, but rather with only a single coil and without the need to orthogonalize impedance components. Sensing of distance (or displacement) using eddy current sensors is another typical application of the present system. Systems that sense distance either sense a change in inductance, resistance, or a combination of both parameters such as 'Q', where $Q=\omega L/R$. These known systems in general rely on the material properties being constant as they will affect the resultant output signals.

With the present invention it is recognized that, at a particular distance and set of electrical properties, the system's impedance will be a unique point in the complex impedance plane. With certain configurations, the parameters can be resolved into mathematically orthogonal equivalents such that one parameter is a function of another. However other situations preclude such analysis. Regardless, signals indicative of the system's impedance should map to a unique point in the impedance plane for a given variable set. The output signals corresponds to real and imaginary impedance parts, phase and magnitude, or other impedance combination. The variable or parameter set corresponds to thickness and distance or material characteristic and distance.

The scaling parameter given above as $r^2\omega\mu\sigma$ is commonly used in prior art systems as the determining characteristic of the impedance output and is appropriate for certain materials. While the parameters $r,\omega,\mu,\sigma$ still determine the impedance characteristic, it is not quite correct to use the product alone as the scaling parameter where the relative permeability of the material is not unity. This represents a complicating factor which is difficult to express in analytic terms and is most often optimized by numerical analysis.

Consequently, the present system can readily be used in the steel roller runout and can thickness applications noted above. The present system allows for the measurement of steel roller runout which is insensitive to permeability changes in the roller. Can thickness is ascertained simultaneously with a measurement of the centerline position of the punch with the present system and therefore may be used to help control thickness as well as correct for apparent thickness errors caused by position changes in the punch.

Figure 1:
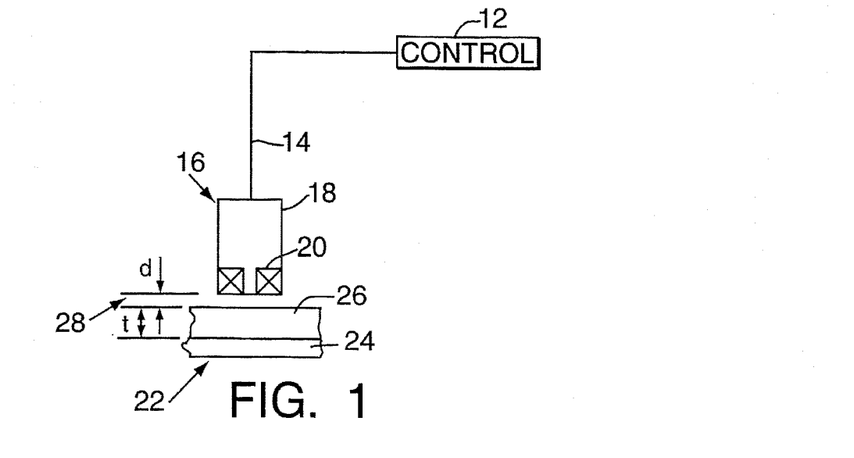
FIG. 1 is a simplified schematic illustration of a system provided according to the present invention.

A system with a sensor configuration provided according to the present invention is shown schematically in FIG. 1. The system 10 includes electronic control circuitry shown generally at 12 which provides an excitation signal on line 14 to a sensor 16 comprised of a sensor body 18 and a sensor coil 20 disposed at an end thereof. The sensor coil is positioned adjacent a workpiece 22 that includes a substrate 24 and outer cladding 26. The system can be configured to measure the "lift-off" 28 corresponding to the separation between the sensor and the workpiece.

The impedance change of the sensor is a function of several parameters including the excitation signal frequency ($\omega$), the mean radius of the sensor coil (r) and the conductivity of the target material ($\sigma$). Those skilled in the art will note that conductivity is simply $1/\rho$, where "$\rho$" or "rho" is resistivity. The permeability of the target material ($\mu$), and the distance to the target (d) are also factors. If frequency and diameter are fixed then the impedance will vary due to $\sigma,\mu$ or d. For a given diameter of sensor coil, a frequency can be found by using known numerical methods such that the coil is sensitive to a combination of $\sigma$ and $\mu$ and d. This frequency can be changed such that $\sigma,\mu$ parameter combination primarily effects the phase of the complex impedance, while d primarily effects the magnitude of the complex impedance output and, as such, are independent of each other. For materials where the relative permeability is unity, that is; $\mu_r=1$, the coil frequency is related to the product of $\sigma$ and $\mu$ and d. The "combination" of $\sigma$ and $\mu$ and d in those other situations optimized with numerical methods is referred herein as the "effective product". As noted above, the real and imaginary parts of the impedance are related mathematically to the phase and magnitude of the impedance outputs and, therefore, either variable can be used. It is not a requirement that a specific frequency be found, however, as the two effects can be sorted out mathematically and, in general, it is desirable to do so.

The present invention also allows for temperature compensation. If the materials parameters (e.g., thickness,$\sigma$ or $\mu$) are constant, then variations in temperature will cause the sensor coil series resistance to change proportionally. The resistance change appears as a change in the real part of the complex impedance. Correcting for temperature changes can therefore be done by recognizing that a unique temperature and distance will also map to a unique point on the complex impedance plane. The above techniques are used to correct distance measurements for changes in temperature.

Figure 2:
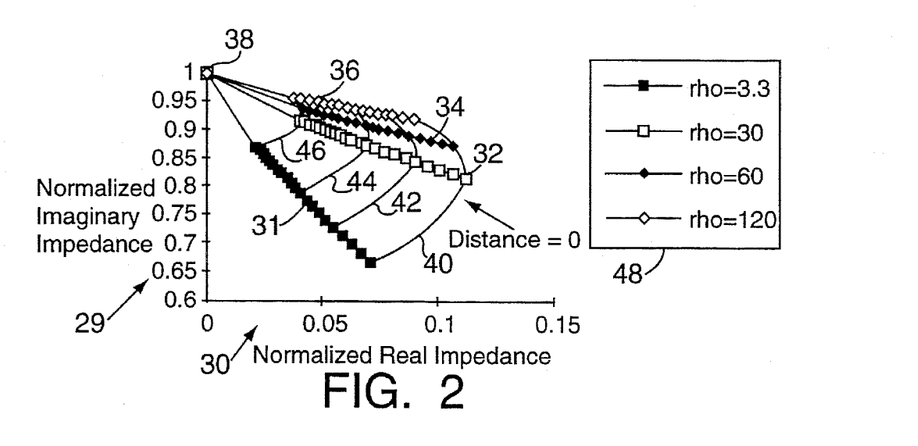
FIG. 2 is a diagrammatic illustration of the effect of electrical properties and distance on normalized impedances using an algorithm executed by the system of FIG. 1.

FIG. 2 is a diagrammatic illustration of the effect of electrical properties and distance on normalized impedances using known methods of numerical analysis. Vertical axis 29 corresponds to the normalized imaginary coil impedance while horizontal axis 30 corresponds to the normalized real impedance of the sensor coil. Curves 31–36 shown in FIG. 2 are for specific cases of $r,\sigma,\mu,\omega$ and d (displacement). Distance is set to infinity at point 38, while curves 40–46 correspond to lines of constant displacement. Set forth in caption 48 are the values of rho expressed in $\mu\Omega$ cm for each of the several material curves The following steps should be executed to generate the appropriate impedances. First, the specific parameter pair or "goal" of the measurement needs to be determined as follows:

1) Generate a displacement output signal independent of material (material insensitivity);
2) Generate an output signal proportional to the resistivity of the material;
3) Generate output signals of resistivity and displacement;
4) Generate an output signal proportional to permeability;
5) Generate output signals proportional to permeability and displacement;
6) Generate an output signal proportional to thickness; or
7) Generate output signals proportional to thickness and displacement;
8) Generate output signals proportional to temperature and displacement;
9) Generate output signals proportional to temperature and $\sigma\mu$ effective product.

There are other supplemental, considerations in finding an optimum solution once one of the above parameter pairs has been chosen. A gross change in parameters, such as completely different materials, is an example of a supplemental consideration, as is the situation where the correction is for small changes in parameters, such as in alloys of the same material. In the example shown with respect to FIG. 2, the present system provides a sensor which is effective with Aluminum (rho=3.3$\mu\Omega$ cm), Hafnium (rho=30$\mu\Omega$ cm), Stainless Steel (rho=60$\mu\Omega$ cm), and Inconel (rho=120$\mu\Omega$ cm). The present system as configured to generate the curves of FIG. 2 generates a linear displacement output signal from 0 to 0.040" in thickness that is independent of the workpiece material and provides information as to the identity of the material. It should be noted that the teaching of the present invention applies for any one of the parameter pairs mentioned above, as well as for other conductive materials.

Selection of a particular coil geometry is also mandated by the present system. It is generally desirable that the coil be of a small diameter, high "Q", and is amenable to cost effective production. The coil geometry used to generate the curves of FIG. 2 has an inner radius of 0.0675 inches, and outer radius of 0.15", a length of 0.1 inches with 640 turns of magnet wire. These variables are provided to the present system to generate the impedance plane. A specific frequency ($\omega$) must be chosen so as to have sensitivity to the electrical parameters, have good sensitivity to displacement, and have a reasonably linear output. With the present system it is not required to have linearity in output signal generation, but it simplifies post processing of the output signal. A typical frequency for the signal is between 5 kHz and 10 Mhz. The frequency parameter is iterated by an algorithm executed by the present system until all of the system parameters have acceptable sensitivity. The algorithm used is one that implements known equations using numerical methods. The output from the algorithm is then plotted to show the real and imaginary relationship with different parameters of displacement and resistivity.

Note in FIG. 2 that for a given coil geometry at a constant temperature, frequency, displacement (or lift-off), and resistivity/permeability combination that there is a unique point in the impedance plane which define the curves of constant displacement (lift-off)). Given that only two of the unknown parameters vary (i.e. resistivity/permeability and displacement, thickness and displacement) it is typical that a coil geometry and operating frequency can be found such that a unique point on the impedance plane maps to a given set of output parameters such as displacement and resistivity.

Figure 3:
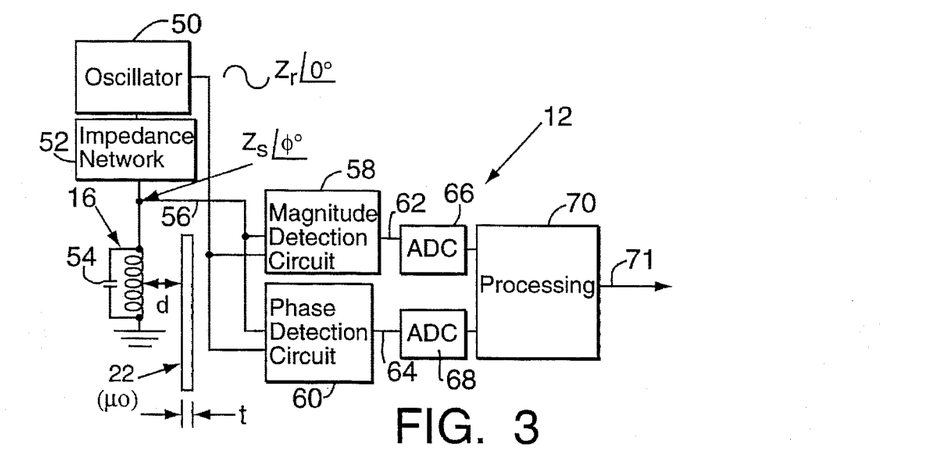
FIG. 3 is a more detailed schematic illustration of the electrical circuitry of the system of FIG. 1.

The preferred embodiment of the present invention shown in FIG. 1 is illustrated schematically in more detail in FIG. 3. The system electronic circuitry 12 consists of an oscillator 50 which drives an impedance network 52, the eddy current sensor 16 and typically a parallel resonating capacitor 54. The oscillator is driven at a predetermined frequency ($\omega$) and amplitude ($Z\angle 0°$) as measured at 0 degrees to excite the impedance network, typically through a series capacitor. The impedance network, parallel capacitance, and oscillator frequency are chosen to optimize the change in magnitude and phase of the drive signal at the sensor ($Z_s\angle \phi°$) relative to the oscillator based on the goals of the measurement as set forth above. A detection signal is presented on line 56 for demodulation by magnitude detection circuit 58 and phase detection circuit 60 to produce independent magnitude and phase output signals on lines 62, 64, respectively. These signals are presented to analog to digital converters 66 and 68 before presentation to processor 70 so that the signals used for processing are independent magnitude and phase output signals from the sensor. These signals are then processed to provide either a digital or analog output signals on line 71 that relate to one or more of the parameters being measured. It is understood by those skilled in the art that analog processing could be utilized as well.

The impedance network and the parallel capacitance are chosen such that the resultant sensor impedance has components which translate into the phase and magnitude plane. In the general case it is not a requirement that the measured effects be orthogonal in the phase and magnitude plane. Rather, it is necessary that these components of impedance map to a unique point in that plane where a look up table or numerical methods can be used to translate phase and magnitude coordinates to resistivity (or other parameter such as thickness) and displacement. With numerical analysis however, the resonant capacitance and the impedance network can be selected such that the phase and magnitude of the output signals have specific characteristics such as linearity in displacement, relative temperature stability, and are mostly orthogonal. If the phase and magnitude characteristics are orthogonal, then processing is much easier as the two signals are essentially independent. As an example, one output signal is related to distance and the other is related to the material characteristics. It is more likely however, that a solution can be obtained in which one parameter is substantially independent and the other parameter has a dependency on that independent parameter; a situation in which a solution is much more readily achieved than its alternatives.

Figure 4:
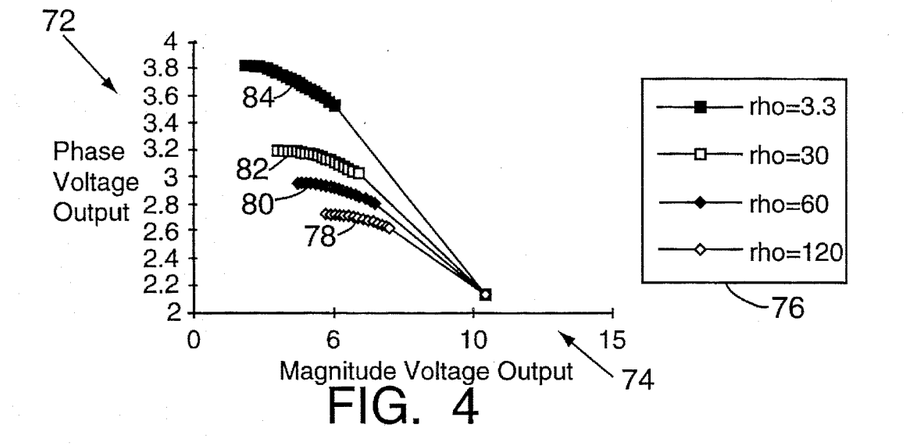
FIG. 4 is a diagrammatic illustration of output signals of the system of FIG. 1.
Figure 5:
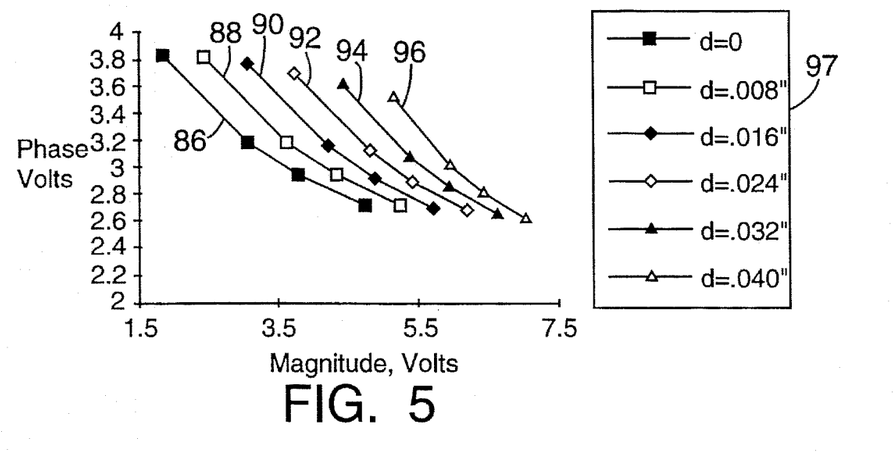
FIG. 5 is a second diagrammatic illustration of the output signals of FIG. 4 replotted as a family of displacement curves.

To generate the curves shown in FIGS. 4 and 5, the impedance network is a series resistor (100 ohm) and capacitor (1250 pF). The parallel capacitor is 5000 pF and the sensor is as set forth above, with a DC resistance of 45 ohms. This configuration results in the displacement measurement appearing mainly in the voltage magnitude of the output signal and the effect of the resistivity occurring mainly as the phase voltage. In FIG. 4, axis 72 corresponds to the phase voltage, while axis 74 displays the voltage magnitude of the output signal. Caption 76 illustrates the different materials by their respective values of resistivity. Curves 78–84, therefore, show the displacement as function of resistivity. The same data can be replotted as a family of displacement curves 86–96 shown in FIG. 5 with caption 97 identifying the curves by material thickness. Here again, a unique point in the phase and magnitude plane translates to a unique displacement and resistivity.

Figure 6:
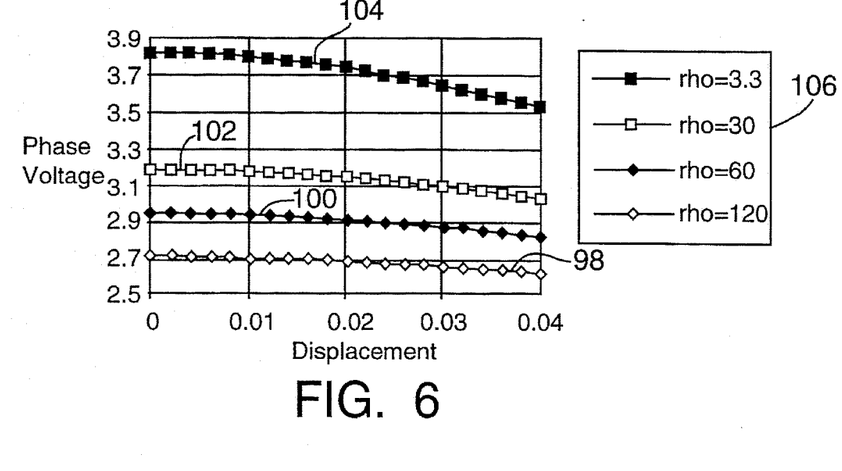
FIG. 6 is a diagrammatic illustration of a family of displacement curves formed by phase voltages measured at several sensor displacements from a workpiece surface.

Shown diagrammatically in FIG. 6 are a family of displacement curves 98–104 formed by phase voltages measured at several displacements. Caption 106 indicates the resistivity of each material. Note that the phase of the output signal for the materials is relatively, but not completely, independent of displacement. In order to sort and identify the material(s) under test, a simple voltage comparator circuit can be added to the processor circuitry of the preferred embodiment.

Figure 7:
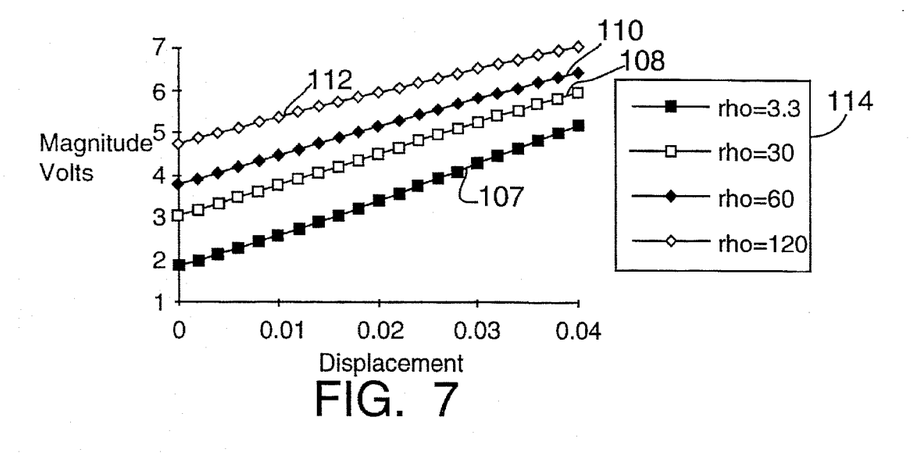
FIG. 7 diagrammatically illustrates the voltage magnitude of output signals provided by the present system as compared to sensor displacement from a workpiece.

FIG. 7 diagrammatically illustrates the voltage magnitude of the output signals as compared to the sensor displacement. The output signals of curves 107–112 are characterized by an offset shift vs. the various materials whose resistivies are shown in caption 114. Using the information from the phase voltage to determine the material, the present system generates an offset correction signal in a known manner that is added to the signals of curves 107–112 to produce a relatively material independent displacement output signal, while simultaneously producing an output signal that identified the material.

The present invention encompasses alternative embodiments to the system described above. As noted above, a punch is used in a can making process to draw an aluminum cup through a series of dies to form a finished can body. The punch thickness changes slightly over long periods of time relative to thickness changes in the can caused by die wear and other factors. Besides the can thickness, it is also desirable to know the centerline running position of the punch during this process. The sensor configuration shown in FIG. 8 accomplishes both measurements simultaneously with some advantages over the sensor configuration described with respect to FIG. 1.

Figure 8:
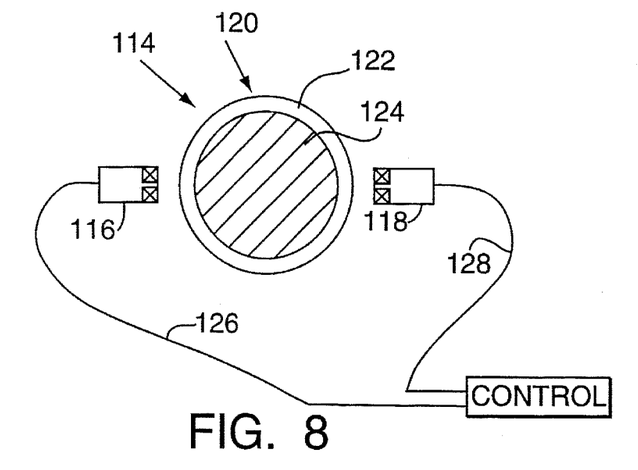
FIG. 8 is a simplified diagrammatic illustration of a differential sensor assembly which comprises part of an embodiment of the present invention alternative to that shown in FIG. 1.

Shown in FIG. 8 is a differential sensor assembly 114 comprised of opposed sensors 116, 118 which are facing a substrate 120 shown in section. The substrate is comprised of cladding 122 that is received on an outer surface of punch 124. The sensor output signals presented on lines 126, 128 corresponds to displacement and are derived from the voltage magnitude of the respective output signals. These signals are combined differentially to produce a single differential output signal that is used to measure the centerline position of the punch. The present invention is advantageous in this regard since differential output signals are more insensitive to the presence or absence of the can and, therefore, provides a better measurement of punch centerline position. The differential sensor embodiment of FIG. 8 also provides a more temperature stable and orthogonal output signal of sufficient magnitude for use in lift-off correction of the phase output signals used to measure thickness.

Figure 9:
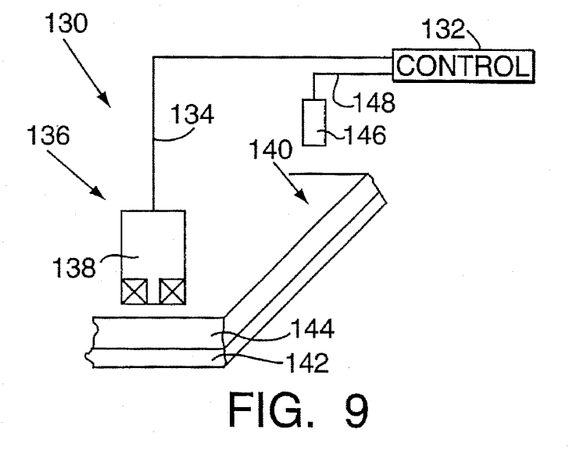
FIG. 9 is a simplified schematic illustration of an alternative system provided according to the present invention characterized by dual sensors.

FIG. 9 is a simplified schematic illustration of a sensor system provided in accordance with the present invention. The system 130 is substantially the same as that shown with respect to FIG. 1 and includes control circuitry 132 which provides an excitation signal on line 134 to a sensor 136.

Within the sensor is a sensor coil 138 disposed at an end adjacent a workpiece 140. The workpiece includes a substrate 142 and outer cladding 144.

Also included in the system is a second sensor 146 which receives excitation signals on line 148 from the controller. The sensor 146 is disposed a distance from the workpiece and therefore is not influenced electromagnetically by its presence. However, the second sensor is positioned so that it is in substantially the same environment as the first sensor and should, therefore, be at the same temperature at the same time as the first sensor. Accordingly, the sensors' respective signals can be used to remove any drift in signal value caused by thermal variations in the temperature. The signal from the second, remote coil is received by the controller. Circuitry with the controller provides a compensation term achieved by the comparison of the impedance of the second coil signal as compared to the signal from the first coil close to the substrate surface. Any drift in signal in the first sensor caused by temperature variations will therefore be eliminated. With this configuration, the present invention uses multiple coils, but not in the same manner as has been utilized in prior art devices. Rather than use a coil pair comprised of excitation and sensor coils as is done in the past, the present invention merely uses a second coil for thermal compensation purposes.

Figure 10:
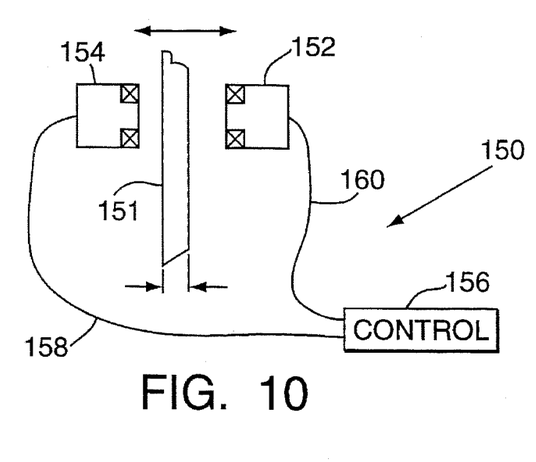
FIG. 10 is a simplified schematic illustration of a second alternative system provided according to the present invention characterized by dual sensors operated differentially to determine workpiece position.

FIG. 10 is a simplified schematic illustration of a second alternative system 150 provided according to the present invention characterized by dual sensors operated differentially to determine the position of workpiece 151. In system 150, sensors 152 and 154 communicate with controller 156 via lines 158, 160. The sensors 152, 156 are operated in a differential manner to generate first and second signals indicative of workpiece position relative to the sensors. The magnitude of the signal received from sensor 152 is subtracted from magnitude of the signal from sensor 154. Signals indicative of workpiece thickness are primarily related to the phase output from each sensor. The thickness signals are then corrected by the controller for errors due to position by the differential magnitude signal. The position output of this alternative system is less dependent on thickness and temperature when the second sensor is used in this manner.

Similarly, although the invention has been shown and described with respect to a preferred embodiment thereof, it should be understood by those skilled in the art that various other changes, omissions and additions thereto may be made therein without departing from the spirit and scope of the present invention.

I claim:

1. A method of measuring physical parameters characteristic of a workpiece whose workpiece parameters include material, thickness, temperature, permeability and conductivity, said method comprising the steps of:

providing an excitation circuit having electrical components that characterize system electrical parameters, said excitation circuit further having an excitation circuit impedance defined by said system electrical parameters;

providing said excitation circuit with a sensor having an electrical coil at a preselected diameter;

positioning said coil at a selected separation distance from said workpiece;

presenting said coil with an excitation signal at a single angular frequency selected such that an effective product of said workpiece permeability and resistivity and said separation distance map to a single point in an excitation circuit impedance plane;

measuring a voltage magnitude of said excitation signal;

measuring a phase of said excitation signal;

generating signals indicative of said single excitation circuit impedance plane point; and generating signals indicative of a computed value of a desired one of said parameters.

2. The method of claim 1 further comprising the steps of:

presenting said coil with an excitation signal at a single preselected angular frequency selected such that an effective product of said workpiece permeability and conductivity effects only the imaginary component of said impedance and the magnitude of said separation distance effects only the real component of said impedance; and generating signals indicative of a computed value of said workpiece permeability and conductivity product.

3. The method of claim 2 further comprising the steps of providing said workpiece from different materials and generating signals indicative of said workpiece permeability and conductivity effective product.

4. The method of claim 2 further comprising the steps of positioning said workpiece at a plurality of separation distances and generating, at each of said separation distances, signals indicative of said workpiece permeability and conductivity effective product.

5. The method of claim 3 further comprising the steps of:

positioning said workpiece at a plurality of separation distances;

generating, at each of said separation distances, signals indicative of said workpiece permeability and conductivity product; and generating signals indicative of displacement independent of selected workpiece material.

6. The method of claim 2 further comprising the steps of selecting said workpiece to be of a plurality of thicknesses and generating, at each of said thicknesses, signals indicative of said workpiece permeability and conductivity effective product.

7. The method of claim 6 positioning said workpiece at a plurality of separation distances and generating, at each of said separation distances, signals indicative of said workpiece permeability and conductivity product and thickness.

8. A system for measuring physical parameters characteristic of a workpiece whose workpiece parameters include material, thickness, temperature, permeability and conductivity, said system comprising:

an excitation circuit having electrical components that characterize system electrical parameters, said excitation circuit further having an excitation circuit impedance defined by said system electrical parameters;

a sensor having a single electrical coil at a preselected diameter electrically connected to said excitation circuit;

a means for positioning said coil at a selected separation distance from said workpiece;

signal generator means for presenting said coil with an excitation signal at a single preselected angular frequency selected such that an effective product of said workpiece permeability and resistivity and said separation distance map to a single point in an excitation circuit impedance plane;

a means for measuring a voltage magnitude of said excitation signal;

a means for measuring a phase of said excitation signal; and processor means for generating output signals indicative of a desired one of said parameters.

9. The system of claim 8 wherein said signal generator means further comprises a means for generating signals indicative of an effective product of said workpiece permeability and conductivity effects only the imaginary component of said impedance and the magnitude of said separation distance effects only the real component of said impedance and wherein said processor further comprises a means for generating signals indicative of a computed value of said workpiece permeability and conductivity effective product.

10. The system of claim 9 wherein said workpiece is selected from different materials; said processor means further comprising a means for generating signals indicative of said workpiece permeability and conductivity effective product.

11. The system of claim 9 further comprising a means for positioning said workpiece at a plurality of separation distances and said processor means further comprises a means for generating, at each of said separation distances, signals indicative of said workpiece permeability and conductivity effective product.

12. The system of claim 10 further comprising:
 a means for positioning said workpiece at a plurality of separation distances; and said processor further comprises
 a means for generating, at each of said separation distances, signals indicative of said workpiece permeability and conductivity product; and
 a means for generating signals indicative of displacement independent of selected workpiece material.

13. The system of claim 10 wherein said workpiece is selected to be of a plurality of thicknesses and said processor means further comprises a means for generating, at each of said thicknesses, signals indicative of said workpiece permeability and conductivity effective product.

14. The system of claim 13 further comprising a means for positioning said workpiece at a plurality of separation distances and said processor means further comprises a means for generating, at each of said separation distances, signals indicative of said workpiece permeability and conductivity product and thickness.

15. The system of claim 9 wherein said workpiece is selected to be a composite of an outer cladding and inner substrate.

16. The system of claim 9 further comprising:
 a second sensor having a coil receiving said excitation signal;
 a means for positioning said sensors with said coils in opposed relation to one another about said workpiece; and
 a means associated with said processor means for differentially processing said measured excitation voltage and phase signals to generate signals indicative of a displacement of said workpiece from a central workpiece position between said sensors.

17. The system of claim 9 wherein said controller further comprises means for orthogonalizing said electrical parameter signals.

18. The system of claim 16 wherein said workpiece is comprised of an outer cladding and inner substrate.

19. The system of claim 9 further comprising means for providing said workpiece at a plurality of temperatures and said processor means further comprising a means for generating, at each of said temperatures, signals indicative of said workpiece permeability and conductivity effective product.

20. The system of claim 9 further comprising:
 a second sensor means substantially identical electrically with said first sensor and positioned to be electromagnetically removed from said workpiece but in thermodynamic communication with said first sensor;
 said processor further comprising a means for generating signals indicative of said first and second sensors temperature values and a means for subtracting said second sensor temperature signal from said first sensor temperature signal, thereby removing temperature drift signals from said output signals.

21. The system of claim 9 wherein said workpiece is nonplanar.

* * * * *